United States Patent [19]

Kaufman et al.

[11] Patent Number: 4,826,773

[45] Date of Patent: May 2, 1989

[54] METHOD AND REAGENT FOR THE QUANTITATIVE DETERMINATION OF PHOSPHOROUS IN SERUM AND URINE

[75] Inventors: Richard A. Kaufman, Belleville; Henry J. Rosenfeld, Florham Park; Denise Zaunczkowski, Wallington, all of N.J.

[73] Assignee: Hoffmann-La Roche Inc., Nutley, N.J.

[21] Appl. No.: 220,772

[22] Filed: Jul. 18, 1988

[51] Int. Cl.$^4$ ............................ G01N 21/78; G01N 33/52
[52] U.S. Cl. .................................. 436/105; 436/103; 436/164
[58] Field of Search ................ 436/103, 105, 164, 166

[56] References Cited

U.S. PATENT DOCUMENTS

| | | | |
|---|---|---|---|
| 3,795,484 | 3/1974 | Daly et al. | 436/105 X |
| 3,796,543 | 3/1974 | Kamphake | 436/103 |
| 3,853,469 | 12/1974 | Morin et al. | 436/105 |
| 3,874,853 | 4/1975 | Byrnes | 436/105 |
| 3,953,359 | 4/1976 | Gindler | 436/105 |
| 4,009,004 | 2/1977 | Hutchinson | 436/105 |
| 4,220,451 | 9/1980 | Stephanchik | 436/105 |
| 4,447,544 | 5/1984 | Neri et al. | 436/105 |
| 4,599,316 | 7/1986 | Hahn et al. | 436/105 |
| 4,731,331 | 3/1988 | Shu et al. | 436/105 X |

FOREIGN PATENT DOCUMENTS 0020875  7/1975  Japan .................................. 436/105

OTHER PUBLICATIONS

Daly et al, Clin. Chem., vol. 18, No. 3, pp. 263–265, 1972.

*Primary Examiner*—Robert J. Hill, Jr.
*Attorney, Agent, or Firm*—Jon S. Saxe; Bernard S. Leon; Matthew Boxer

[57] ABSTRACT

A reagent for determining quantitatively the amount of phosphorous in bodily fluids which comprises a surface active agent, a strong acid, ammonium molybdate, a heavy metal chelating compound, and anti-oxidant, and deionized water is described. A method of using such a reagent is also described.

10 Claims, No Drawings

METHOD AND REAGENT FOR THE QUANTITATIVE DETERMINATION OF PHOSPHOROUS IN SERUM AND URINE

BACKGROUND OF THE INVENTION

The determination of the amount of phosphorous in bodily fluids such as serum or urine is important since determination of a build-up of phosphorous in bodily fluids can allow for the diagnosis of diseases such as uremia and chronic renal diseases where phosphorous retention occurs.

Quantitative determination of phosphorous in bodily fluids has been conventionally performed photometrically by use of the molybdenum blue reaction (I.M. Kolthoff and P.D. Elving. editors. part II, Volume V pages 317–402 1961). This reaction involves the formation of a phosphate molybdate complex which is then reduced by means of a reducing agent selected from the group consisting of phenylhydrazine, ascorbic acid, amino naphthol sulfonic acid or other reducing agents. Upon reduction, a blue colored complex of heteropolyacid is formed and absorbance of this complex is measured at around 700 nanometers.

Several disadvantages are associated with this conventional method for quantitatively determining the phosphorous in bodily fluids. First, it is necessary to have a protein free serum sample in order to perform this test, and preparation of such a protein free serum sample is cumbersome. Secondly, the sensitivity of this test is low. Finally, in order to perform this test, two sequential additions of reagent are required. That is, first the phosphate molybdate complex is formed, and then as-noted above it is reduced. Such a two step process reduces the speed with which quantitative tests for phosphorous can be performed. Since the emphasis is for the quick and accurate completion of many tests, this latter disadvantage is particularly serious.

An attempt to overcome this latter disadvantage is disclosed in U.S. Pat. No. 3,795,484 which discloses a phosphorous determination which involves measurement of the unreduced phosphomolybdate complex at around 340 nanometers.

More specifically, this process of U.S. Pat. No. 3,795,484 comprises the steps of (a) forming a mixture of the phosphate containing fluid and an ammonium molybdate solution;

(b) measuring by means of a centrifugal analytical photometer, a first absorbance reading at 340 nanometers within two seconds after said mixture is formed;

(c) measuring a second absorbance reading at 340 nanometers within ten minutes after said mixture is formed;

(d) comparing the absorbance differential with at least one other differential obtained simultaneously under the same conditions from a fluid containing a known concentration of phosphorous, and (e) determining the amount of phosphorous in the phosphate containing fluid.

Several disadvantages are associated with this process. First, the process requires that the first absorbance reading must be obtained within two seconds of mixing the reagent with the sample of bodily fluid. Such a limitation makes this prior art process cumbersome to perform. Second, because there exists a difference between the matrices of protein (e.g., serum) and aqueous-based samples that causes the protein-based samples to react faster than aqueous samples, this prior art process requires a separate calibration for a phosphorous determination on an aqueous sample of bodily fluid such as urine and a protein sample of bodily fluid such as serum.

It is an object of the present invention to provide a process for the quantitative determination of phosphorous in bodily samples which involves a photometrically measured molybdate forming reaction which proceeds slowly enough so that the first of two absorbance readings may be taken as late as ten seconds after reagent is mixed with the bodily fluid to be tested.

It is another object of the present invention to provide a process for the quantitative determination of phosphorous in bodily fluids such that the same calibration can be used whether an aqueous bodily fluid such as urine or a protein-based bodily fluid such as serum is tested. By providing such a process, one would be able to run aqueous and serum samples for a quantitative determination of the phosphorous simultaneously.

BRIEF SUMMARY OF THE INVENTION

The invention relates to a process and reagent for quantitatively determining phosphorous in bodily fluids which comprises a surface active agent, a strong acid, ammonium molybdate which is $(NH_4)_6Mo_7O_2.4H_2O$, a heavy metal chelating compound, an anti-oxidant, optionally an antifoaming agent and deionized water. Through the process and reagent kit of the invention, there is provided a quantitative phosphorous determination which involves two photometric absorbance readings. the first of which can take place as late as ten seconds after the mixing of the bodily fluid with the reagent. Also, through the process of the present invention, there is provided a means for determining phosphorous in bodily fluids such that either an aqueous bodily fluid such as urine or a protein-based bodily fluid such as serum can be run without changing the calibration.

DETAILED DESCRIPTION OF THE INVENTION

This invention relates to a process for the quantitative determination of phosphorous in bodily fluids. This invention also relates to a reagent for carrying out a quantitative determination of the phosphorous in bodily fluids. By this invention, there is provided a quantitative determination of phosphorous which involves the photometric reading of absorbances caused by the formation of a phosphomolybdate complex wherein the first such absorbance reading can be taken as late as ten seconds after the mixing of the bodily fluid and reagent since the reagent is such that the formation of the phosphomolybdate complex is markedly slower than in prior art processes for a photometric guantitative determination of phosphorous.

Also by this invention, there is provided a process and a reagent for determining quantitatively the phosphorous in bodily fluids wherein either an aqueous bodily fluid such as urine or a protein-based bodily fluid such as serum may both be measured using the same calibration.

Quantitative determination of phosphorous in bodily fluids is important in the diagnosis of several diseases such as uremia and chronic renal diseases where phosphorous retention occurs.

The reagent of the invention determines only the quantity of the so-called inorganic phosphates in bodily fluids. Whenever the specification refers to concentrations or amounts of phosphorous, this means the phosphorous that is in these inorganic phosphates.

The significance of changes in organic phosphorous such as, phospholipids, phosphate esters and nucleotide phosphate, is, in fact, not easily related to clinical problems.

The reagent of invention is made up as described just below. The concentrations given are the concentrations for the particular ingredients after the reagent has been fully formulated. Sulfuric acid in the concentration of about 0.675 M to about 1.25 M is added to a solution containing about 0.01% W/V to about 5% W/V of surface active agent, about 0.001% W/V to about 0.5% W/V of N-hydroxyethylethylenediaminetriacetic acid which is a heavy metal chelating compound, and about 0.0001% W/V to about 0.01% W/V butylated hydroxyanisole which is an antioxidant, in deionized water. To this, ammonium molybdate in the concentration of about 1.75 mM to about 6.25 mM is added, and then optionally there is finally added an anti-foaming agent in the range of about 0.001% to about 0.1% W/V.

As used herein M means moles per liter; mM means millimoles per liter; and % W/V means grams per 100 ml of solution. Accordingly, 0.01 grams in 100 ml of solution is 0.01% W/V. Similarly, 0.5 grams in 100 ml of solution is 0.5% W/V.

The surface active agent of the reagent of the invention must be such that serum and aqueous bodily fluids of the same phosphorous concentrations give the same absorbance readings. The surface active agent of the reagent of the invention must also prevent the precipitation of protein from the bodily fluids tested. An example of such a surface active agent is the nonionic surface active agent polyoxyethylene (23) lauryl ether which has the chemical formula $C_{12}H_{25}(OCH_2CH_2)_{23}OH$. Particularly preferred as a surface active agent is the nonionic surface active agent polyoxyethylene (20) oleyl ether which has the chemical formula $C_{18}H_{35}(OCH_2CH_2)_{20}OH$.

Exemplary of a heavy metal chelating compound is citric acid, or more especially, N-hydroxyethylethylenediaminetriacetic acid.

The anti-oxidant of the reagent of the invention may be any anti-oxidant which will prevent the oxidation of the surface active agent. particularly preferred as an anti-oxidant is butylated hydroxyanisole.

The strong acid of the reagent of the invention may be most acids which are almost totally ionized in water solution. Exemplary of strong acids are alkyl and aromatic sulfonic acids and especially alkylsulfonic acids such as methanesulfonic acid and ethanesulfonic acid and arylsulfonic acids like phenylsulfonic acid and naphthalenesulfonic acid. Benzoic acids like trinitrobenzoic acid may also be used. Other strong acids include, hydrochloric acid, trifluoroacetic acid, fluoboric acid, hydroiodic acid, sulfurous acid, iodic acid, periodic acid, selenic acid, oxalic acid, maleic acid, dichloroacetic acid, and cyclopropane 1,1 dicarboxylic acid. Especially preferred as a strong acid in the reagent of the invention is sulfuric acid.

A particular reagent of the invention was prepared as follows:

One liter of reagent was made by first dissolving seven grams of Brij ®99, 0.01 grams of butylated hydroxyanisole and 0.15 grams of N-hydroxyethylethylenediamine triacetic acid in about 500 milliliters of deionized water. To this was added 41.7 milliliters of concentrated sulfuric acid. Ammonium molybdate in the amount of 2.55 grams was then dissolved in the reagent and finally 100 microliters of the anti-foaming agent, Colloid 1010 was added. Sufficient additional deionized water was added so that the total volume of reagent was 1 liter.

The surface active agent used in preparing in the above example, Brij ®99 is polyoxyethylene (20) oleyl ether with the Chemical Formula $C_{18}H_{35}(OCH_2CH_2)_{20}OH$, the Formula Weight 1149.56, and the Melting point 25°–30° C.

Colloid 1010, is sold by Colloids, Inc. of 394 Frelinghuysen Avenue, Newark, N.J. 07114. Colloid 1010 is a silicone based foam control agent with the following typical properties:

| | |
|---|---|
| Appearance: | Opaque, stable liquid |
| Color: | White |
| Type: | Stable Emulsion |
| Non Volatile Residue @ 105° C.; %: | 15.0 |
| Specific Gravity @ 25° C.; %: | 1.0 |
| Silicone fluid content; % | 10.0 |

In order to avoid foaming problems, an antifoaming agent is included in a preferred embodiment of the reagent of the invention.

A reagent of the invention can be formulated with ingredients in the following concentrations. The concentrations given are the concentrations for the partcular ingredients after the reagent has been fully formulated.

Sulfuric acid in the concentration of about 0.675 M to about 1.25 M is added to a solution containing about 0.01% W/V to about 5% W/V of surface active agent, about 0.001% W/V to about 0.5% W/V of N-hydroxyethylethylenediaminetriacetic acid, and about 0.0001% M/V to about 0.01% W/V butylated hydroxyanisole in deionized water. To this, ammonium molybdate in the concentration of about 1.75 mM to about 6.25 mM is added, and then optionally there is finally added an anti-foaming agent in the range of about 0.001W/V to about 0.1% W/V.

The advantages of the reagent of the invention are as follows. The reagent of the invention is a single reagent mixture as compared to the two reagent mixtures of the prior art. Accordingly, no pretest mixing is required for the reagent of the invention.

In addition, the reaction of sample with the reagent of the invention is somewhat slower than prior art reagents and accordingly up to 10 seconds can elapse before the first absorbance reading is taken. Therefore it is more convenient than prior art methods for obtaining a phosphorous measurement such as in U.S. Pat. No. 3,795,484 wherein the first absorbance measurement is taken within two seconds after the mixture of reagent and sample is formed. As noted above, in the present invention the first absorbance reading can be taken up to 10 seconds after mixing the reagent and sample, preferably, the first absorbance reading is taken about 4.5 seconds after mixing the reagent and sample.

Finally, a critical advantage of the present invention over the prior art is that both aqueous and serum samples may be assayed together with the need for only one calibration, which can be with either an aqueous or a serum standard. This is because although the reaction rates for aqueous and serum samples of equal concentrations differ slightly, the reagent of the invention is such that the change in absorbance of aqueous and serum samples of equal phosphorous concentrations is the same.

The reagent of the invention is designed to be used in any noncentrifugal or centrifugal analytical photometer and especially in the COBAS ™ diagnostic systems BIO ®, FARA ® and MIRA ®.

The amount of phosphorous in a bodily fluid is quantitatively determined in accordance with the process of the invention by forming a mixture of the bodily fluid, the diluent deionized water, and the reagent. The volume ratio of bodily fluid to diluent plus reagent may range from about 1:125 to 1:30, preferably about 1:50. A first absorbance reading at 340 nanometers is then taken. This first absorbance reading may be taken as late as ten seconds after formation of the mixture. This absorbance reading is taken by a non-centrifugal, or more, preferably a centrifugal analytical photometer.

A second absorbance reading is taken within 10 minutes of the formation of the mixture. Because the reaction of bodily fluid and reagent is relatively slow for the reagent of the invention this first absorbance reading may serve as a sample blank.

The difference between the two absorbance readinqs is then compared against absorbances of fluids of known concentrations of phosphorous in order to quantitate the amount of phosphorous in the bodily fluid being tested.

In the tests which follow which demonstrate the efficacy of the reagent of the invention, five microliters of sample, 50 microliters of diluent (deionized water), plus 200 microliters of reagent were added in parallel to their respective compartments on a cuvette rotor of a COBAS BIO ® centrifugal analyzer. The reaction was then monitored at 340 nanometers.

A first absorbance reading was taken at 4.5 seconds after mixing. At this time, only a small amount of the reaction had taken place, thereby allowing the reading to serve as a sample blank. A second reading was then taken at 3 minutes after mixing at which time the reaction was near completion. The concentration of phosphorous was calculated by multiplying the difference between the last and first absorbance readings by a calibration factor which was calculated from standards of known phosphorous concentration.

An absorbance reading taken early in the reaction provides for an auto sample blank which allows for lipemic, icteric and hemolyzed samples to be assayed accurately with no interference.

TEST TO SHOW SAMPLE BLANKING CAPABILITY OF THE REAGENT OF THE INVENTION

The following materials were used in this test.
1. Aqueous Standards

Aqueous standards containing inorganic phosphorous (3,6, and 12 mg/dL phosphorous)

2. Normal human serum - (heat inactivated, filtered, 0.1% azide) - spiked with KH$_2$PO$_4$ (potassium phosphate) to give samples of 1.5, 4, 6, 8, 10, 12, 14, 16 and 18 mg/dL phosphorous.

3. Lipemic and hemolyzed samples.

4. The reagent for inorganic phosphorus described below - (2 reagent system with sample blank).

5. One reagent system of the invention.

The lipemic and hemolyzed patient samples were first assayed using the two reagent system which is known to give a sample blank. With the two reagent system, sample is mixed with a first reagent which contains 0.36 mol/L sulfuric acid and a sample blank absorbance measurement is taken at 340 nanometers. A second reagent which contains 5 4 mmol/L ammonium molybdate is then added and after 15 seconds a second absorbance measurement is taken at 340 nanometers. The first absorbance reading is subtracted from the second absorbance to obtain the net absorbance change due to the phosphorous present in the sample. The same samples were then run using the one reagent system of the invention.

Results

Table I shows comparable results were obtained from lipemic and hemolyzed samples on both the two reagent system described above and the one reagent system of the invention demonstrating that the one reagent system of the invention is comparable, in its accuracy, with a proven prior art assay for phosphorous, which prior art assay includes a sample blank absorbance measurement. Thus Table I shows the sample blanking capability of the reagent of the invention.

TABLE I

|  | Sample # | 2 Reagent | 1 Reagent |
|---|---|---|---|
| Lipemic | 1 | 2.8 mg/dL | 2.3 mg/dL |
|  | 2 | 4.5 | 4.4 |
|  | 3 | 4.1 | 3.9 |
|  | 4 | 3.7 | 3.6 |
|  | 5 | 17.2 | 16.9 |
| Hemolyzed | 1 | 14.7 | 14.3 |
|  | 2 | 3.5 | 3.0 |
|  | 3 | 2.8 | 2.9 |
|  | 4 | 3.9 | 3.8 |

TEST TO SHOW AQUEOUS AND SERUM BASED SAMPLES CAN BE RUN WITH AN AQUEOUS STANDARD

The following materials were used in this test.
1. Aqueous standards containing inorganic phosphorous (3,6, and 12 mg/dL phosphorous).

2. Aqueous Samples - Distilled H$_2$O spiked with potassium phosphate to give samples of 1.5, 4, 6, 8, 10, 12, 14, 16 and 18 mg/dL phosphorous.

3. Serum Samples - normal human serum (heat inactivated, filtered, 0.1% azide) spiked with potassium phosphate to yield samples of 1.5, 4, 6, 8, 10, 12, 14, 16 and 18 mg/dL phosphorous.

4. The reagent for inorganic phosphorous described above - (2 reagent system with sample blank).

5 One reagent system of the invention.

Results

Aqueous and serum samples of similar phosphorous concentrations were run on the COBAS BIO ® with both the 2 reagent system described above and the 1 reagent system of the invention using only aqueous standards to calibrate the instrument.

Table II shows the phosphorous concentrations for the aqueous standards used to calibrate, and the phosphorous concentrations of aqueous and serum samples that were assayed against this calibration curve. Next to each phosphorous concentration is the change in absorbance at 340 nanometers from the first reading at 4.5 seconds to the final reading at 3 minutes. Note that the change in absorbance for aqueous and serum samples of the same or similar phosphorous concentrations are equal or proportional, thus demonstrating that aqueous and serum samples can be run with the reagent of the invention using only an aqueous standard for calibration despite the difference in reaction rates of aqueous and serum samples.

TABLE II

| Aqueous Standard Phosphorous | | Aqueous Sample Phosphorous | | Serum Sample Phosphorous | |
|---|---|---|---|---|---|
| conc. | ΔA | conc. | ΔA | conc. | ΔA |
| | | 1.6 mg/dL | 0.14 | 1.6 mg/dL | 0.14 |
| 3 mg/dL | 0.27 | 3.7 | 0.32 | 3.7 | 0.33 |
| 6 | 0.53 | 5.8 | 0.51 | 5.8 | 0.51 |
| | | 8.3 | 0.73 | 7.8 | 0.69 |
| | | 10.2 | 0.90 | 9.9 | 0.87 |
| 12 | 1.03 | 11.7 | 1.03 | 11.9 | 1.05 |
| | | 13.6 | 1.20 | 13.8 | 1.21 |
| | | 15.3 | 1.35 | 15.7 | 1.38 |
| | | 17.3 | 1.52 | 17.6 | 1.56 |

$\Delta A = A_{3\,min.} - A_{4.5\,seconds}$

TEST TO SHOW THAT AQUEOUS AND SERUM SAMPLES CAN BE RUN WITH EITHER AQUEOUS OR SERUM STANDARDS

The following materials were used in this test:
1. Aqueous standards containing phosphorous (3,6 and 12 mg/dL phosphorous).
2. Human serum sample of known phosphorous level.
3. Normal human serum (heat inactivated, filtered 0 1% azide) spiked with potassium phosphate to yield samples of 1.5, 4, 6, 8, 10, 12 and 14 mg/dL phosphorous.
4. Urine samples diluted 1:10 with deionized water.
5. Normal and lipemic human serum samples.

In performing this test the samples were assayed first with the 2 reagent system described above using aqueous standards for calibration. The same samples were assayed with the one reagent system of the invention, first with calibration by aqueous standards then with calibration by serum standards.

Table III shows that the results from the three different assays correlate very well whether the sample was normal serum, lipemic serum, or urine. Note that the calibration factors for the one reagent system of the invention using either aqueous or serum standards are essentially the same.

Results

TABLE III

| | | 2 Reagent Aqueous Standard | 1 Reagent Aqueous Standard | 1 Reagent Serum Standard |
|---|---|---|---|---|
| Spiked | 1 | 1.1 mg/dL | 1.2 mg/dL | 1.2 mg/dL |
| Normal | 2 | 3.8 | 3.9 | 3.9 |
| Serum | 3 | 5.9 | 5.9 | 6.0 |
| | 4 | 8.2 | 8.1 | 8.0 |
| | 5 | 10.2 | 10.2 | 10.3 |
| | 6 | 12.8 | 12.5 | 12.3 |
| | 7 | 14.5 | 14.3 | 14.4 |
| Urine | 1 | 1.1 | 1.1 | 1.1 |
| | 2 | 0.8 | 0.9 | 0.9 |
| | 3 | 2.4 | 2.5 | 2.5 |
| | 4 | 2.0 | 2.1 | 2.1 |
| | 5 | 4.4 | 4.5 | 4.5 |
| | 6 | 6.0 | 6.1 | 6.2 |
| Normal | 1 | 4.6 | 4.5 | 4.6 |
| Serum | 2 | 4.0 | 4.1 | 4.1 |
| Samples | 3 | 3.8 | 3.9 | 3.9 |
| Lipemic | 1 | 2.9 | 2.5 | 2.5 |
| Serum | 2 | 4.6 | 4.8 | 4.8 |
| Samples | 3 | 3.6 | 3.5 | 3.5 |
| | 4 | 5.1 | 3.9 | 4.1 |
| Calibration | | 9.9 | 11.3 | 11.4 |

TABLE III-continued

| | 2 Reagent Aqueous Standard | 1 Reagent Aqueous Standard | 1 Reagent Serum Standard |
|---|---|---|---|
| Factor | | | |

We claim:
1. A composition for quantitatively determining phosphorous in bodily fluids which comprises a surface active agent at a concentration in the range of about 0.01% W/V to about 5% W/V, a strong acid at a concentration in the range of about 0.675 M to about 1.25 M, ammonium molybdate at a concentration in the range of about 1.75 mM to about 6.25 mM, a heavy metal chelating compound, an anti-oxidant, and deionized water.

2. The composition in accordance with claim 1, wherein the surface active agent is polyoxyethylene (20) oleyl ether of the chemical formula $C_{18}H_{35}(OCH_2CH_2)_{20}OH$.

3. The composition in accordance with claim 1, wherein the strong acid is sulfuric acid.

4. The composition according to claim 3 wherein the heavy metal chelating compound is N-hydroxyethylethylenediaminetriacetic acid at a concentration in the range of about 0.001% W/V to about 0.5% W/V, and the anti-oxidant is butylated hydroxyanisole at a concentration in the range of about 0.0001% W/V to about 0.01% W/V.

5. The composition in accordance with claim 1, which comprises about 7 grams per liter of polyoxyethylene (20) oleyl ether of the chemical formula $C_{18}H_{35}(OCH_2CH_2)_{20}OH$ as the surface active agent, about 41.7 milliliters per liter of concentrated sulfuric acid about as the strond acid, about 2.55 grams per liter of ammonium molybdate, about 0.15 grams per liter of N-hydroxyethylethylenediaminetriactic acid as the heavy metal chelating compound, about 0.01 grams per liter of butylated hydroxyanisole as the anti-oxidant, microliters per liter of an antifoaming agent, and the remainder deionized water.

6. In a process for determining aqueous or serum phoshorous in a phosphorous-containing bodily fluid wherein such determination is made utilizing a centrifugal or noncentrifugal analyzer and wherein a mixture is formed of said phosphorous-containing body fluid and an ammonium molybdate solution in the presence of a surface active agent, the improvement which comprises using polyoxyethylene (20) oleyl ether of the chemical formula $C_{18}H_{35}(OCH_2CH_2)_{20}OH$ as the surface active agent butylated hydroxyanisole, as an anti-oxidant in the mixture, and N-hydroxyethylethylenediaminetriacetic acid, as a heavy metal chelating compound in the mixture.

7. A process for determining quantitatively determining the phosphorous in a bodily fluid which comprises:
(a) forming a mixture of the bodily fluid and a oomposition
which comprises a surface active agent at a concentration in the range of about 0.01% W/V to about 5% W/V, a strong acid at a concentration in the range of about, 0.675 M to about 1.25 M, ammonium molybdate at a concentration in the range of about 1.75 mM to about 6.25 mM, a heavy metal chelating compound, an anti-oxidant and deionized water;

(b) making by means of an analytical photometer, a first absorbance reading at 340 nanometers within 10 seconds after the mixture of step (a) is formed;

(c) making a second absorbance reading at 340 nanometers within 10 minutes after the mixture of step (a) is formed.

(d) comparing the difference between the two absorbance readings with absorbance readings from fluids of known phosphorous concentrations to quantitatively determine the phosphorous of the bodily fluid.

8. The process in accordance with claim 7, wherein the surface active agent is polyoxyethylene (20) oleyl ether of the chemical formula $C_{18}H_{35}(OCH_2CH_2)_{20}OH$.

9. The process in accordance with claim 8, wherein the strong acid is sulfuric acid.

10. The process in accordance with claim 9, wherein the metal chelating compound, is N-hydroxyethylethylenediaminetriacetic acid at a concentration in the range of about 0.001% W/V to about 0.5% W/V, and the anti-oxidant is butylated hydroxyanisole at a concentration in the range of about 0.0001% W/V to about 0.01% W/V.

* * * * *